United States Patent
Aghassian et al.

(10) Patent No.: US 9,026,220 B2
(45) Date of Patent: May 5, 2015

(54) SYSTEM FOR AN IMPLANTABLE MEDICAL DEVICE HAVING AN EXTERNAL CHARGER COUPLEABLE TO ACCESSORY CHARGING COILS

(71) Applicant: Boston Scientific Neuromodulation Corporation, Valencia, CA (US)

(72) Inventors: Daniel Aghassian, Glendale, CA (US); Bob Ozawa, Woodland Hills, CA (US); Joonho Hyun, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/216,950

(22) Filed: Mar. 17, 2014

(65) Prior Publication Data

US 2014/0197786 A1 Jul. 17, 2014

Related U.S. Application Data

(63) Continuation of application No. 13/671,693, filed on Nov. 8, 2012, now Pat. No. 8,682,444.

(60) Provisional application No. 61/578,487, filed on Dec. 21, 2011.

(51) Int. Cl.
*A61N 1/00* (2006.01)
*A61N 1/36* (2006.01)
(Continued)

(52) U.S. Cl.
CPC ........ *A61N 1/36128* (2013.01); *A61N 1/36125* (2013.01); *A61N 1/3787* (2013.01); *H02J 7/025* (2013.01)

(58) Field of Classification Search
CPC ........... A61N 1/36125; A61N 1/36128; A61N 1/3787; A61N 1/37223; A61N 1/37235; H02J 7/025

USPC .......................................................... 607/59
See application file for complete search history.

(56) References Cited

U.S. PATENT DOCUMENTS 5,314,457 A 5/1994 Jeutter et al.
6,505,077 B1 1/2003 Kast et al.
(Continued)

FOREIGN PATENT DOCUMENTS

JP 2004-73725 3/2004
WO 2000/02212 1/2000
(Continued)

OTHER PUBLICATIONS

DS1825 Programmable Resolution 1-Wire Digital Thermometer with 4-Bit ID. PDF file. Apr. 8, 2010. Pages 1-21. Maxim Integrated.
(Continued)

*Primary Examiner* — George Manuel
(74) *Attorney, Agent, or Firm* — Lewis & Reese, PLLC

(57) ABSTRACT

An external charger system is disclosed comprising an external charger with an internal charging coil, as well as an output port coupleable to one of a plurality of types of external accessory charging coils of varying shapes and sizes. If the internal charging coil of the external charger is sufficient for a given patient's charging needs, the accessory charging coils may be detached from the external charger, and the external charger may serve as a standalone self-contained external charger. The external charger can automatically detect which of the plurality of types of accessory charging coils is connected, and can adjust its operation accordingly. This versatile design allows the external charger system to be used by large numbers of patients, even if their particular implant charging scenarios are different.

34 Claims, 7 Drawing Sheets

(51) Int. Cl.
*A61N 1/378* (2006.01)
*H02J 7/02* (2006.01)

(56) References Cited

U.S. PATENT DOCUMENTS

| | | | |
|---|---|---|---|
| 6,516,227 B1 | 2/2003 | Meadows et al. | |
| 6,553,263 B1 | 4/2003 | Meadows et al. | |
| 6,658,300 B2 | 12/2003 | Govari et al. | |
| 7,107,103 B2 * | 9/2006 | Schulman et al. | 607/61 |
| 7,123,206 B2 | 10/2006 | Hess et al. | |
| 7,200,504 B1 | 4/2007 | Fister | |
| 7,286,880 B2 | 10/2007 | Olson et al. | |
| 7,428,438 B2 * | 9/2008 | Parramon et al. | 607/61 |
| 2004/0098068 A1 | 5/2004 | Carbunaru et al. | |
| 2005/0075689 A1 | 4/2005 | Toy et al. | |
| 2005/0113887 A1 | 5/2005 | Bauhahn et al. | |
| 2005/0143781 A1 | 6/2005 | Carbunaru et al. | |
| 2005/0187590 A1 | 8/2005 | Boveja et al. | |
| 2007/0060967 A1 | 3/2007 | Strother et al. | |
| 2007/0060980 A1 | 3/2007 | Strother et al. | |
| 2007/0270921 A1 | 11/2007 | Strother et al. | |
| 2008/0300654 A1 | 12/2008 | Lambert et al. | |
| 2009/0024179 A1 | 1/2009 | Dronov | |
| 2009/0069869 A1 | 3/2009 | Stouffer et al. | |
| 2009/0118796 A1 | 5/2009 | Chen et al. | |
| 2010/0106223 A1 | 4/2010 | Grevious et al. | |
| 2010/0204756 A1 | 8/2010 | Aghassian et al. | |
| 2011/0190849 A1 | 8/2011 | Faltys | |
| 2012/0112691 A1 * | 5/2012 | Kurs et al. | 320/108 |

FOREIGN PATENT DOCUMENTS

| | | |
|---|---|---|
| WO | 2005/032658 | 4/2005 |
| WO | 2007/124325 | 11/2007 |

OTHER PUBLICATIONS

ANS Medical. Implantable Therapies for Chronic Pain & Neurological Disorders; Rechargeable IPG Systems. PDF file. Nov. 2, 2007. Pages 1-5. Advanced Neuromodulation Systems, Inc. Plano, TX, US.

Medtronic, Inc. Medtronic Pain Therapies: Neurostimulators and Their Selection; Rechargeable Neurostimulation System. PDF File. Nov. 2, 2007. Pages 1-4. Medtronic, Inc.

* cited by examiner

SYSTEM FOR AN IMPLANTABLE MEDICAL DEVICE HAVING AN EXTERNAL CHARGER COUPLEABLE TO ACCESSORY CHARGING COILS

CROSS-REFERENCE TO RELATED APPLICATIONS

This is a continuation application of U.S. patent application Ser. No. 13/671,693, filed Nov. 8, 2012 (allowed), which is a non-provisional application of U.S. Provisional Patent Application Ser. No. 61/578,487, filed Dec. 21, 2011. Priority is claimed to these applications, and they are incorporated herein by reference in their entireties.

FIELD OF THE INVENTION

This disclosure relates generally to an accessorized external charger system for a rechargeable implantable medical device, such as Spinal Cord Stimulation (SCS), Deep Brain Stimulation (DBS), occipital nerve stimulation (ONS), peripheral nerve stimulation, and others.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, occipital nerve stimulators to treat chronic headaches, cortical and deep brain stimulators to treat motor and psychological disorders, and other neural stimulators to treat urinary incontinence, sleep apnea, shoulder sublaxation, etc.

FIGS. 1A and 1B show an Implantable Pulse Generator (IPG) 100, which includes a biocompatible case 30 formed of titanium, for example. The case 30 usually holds the circuitry and power source or battery necessary for the IPG to function. The IPG 100 is coupled to electrodes 106 via one or more electrode leads (two such leads 102a and 102b are shown), such that the electrodes 106 form an electrode array 110. The electrodes 106 are carried on a flexible body 108, which also houses the individual signal wires 112a-112p, coupled to each electrode. The signal wires 112a-112p are connected to the IPG 100 by way of an interface 115, which may be any suitable device that allows the leads 102 (or a lead extension, not shown) to be removably connected to the IPG 100. Interface 115 may comprise, for example, an electro-mechanical connector arrangement including lead connectors 38a and 38b configured to mate with corresponding connectors on the leads. In the illustrated embodiment, there are eight electrodes on lead 102a, labeled $E_1$-$E_8$, and eight electrodes on lead 102b, labeled $E_9$-$E_{16}$, although the number of leads and electrodes is application specific and therefore can vary.

As shown in FIG. 2, an IPG 100 typically includes an electronic substrate assembly 14 including a printed circuit board (PCB) 16, along with various electronic components 20, such as microprocessors, integrated circuits, and capacitors, mounted to the PCB 16. Ultimately, the electronic circuitry performs a therapeutic function, such as neurostimulation. A feedthrough assembly 24 routes the various electrode signals from the electronic substrate assembly 14 to the lead connectors 38a, 38b, which are in turn coupled to the leads 102 (see FIGS. 1A and 1B). The IPG 100 further comprises a header connector 36, which, among other things, houses the lead connectors 38a, 38b. The IPG 100 can further include a telemetry antenna or coil (not shown) for receipt and transmission of data to an external device such as a portable or hand-held or clinician programmer (not shown), which can be mounted within the header connector 36. Alternately, in some embodiments, charging coil 18 may be utilized as both a charging coil and a telemetry coil. The IPG 100 usually also includes a power source, and in particular a rechargeable battery 26.

Also shown in FIG. 2 is an external charger 12 that is used to recharge the battery 26 in the IPG 100, which is explained in further detail below. The external charger 12 itself needs power to operate, and therefore may include its own battery 70, which may also be a battery that is rechargeable using a plug-in-the-wall charging cradle or power cord connection, much like a cellular telephone. Alternatively, the external charger 12 may lack a battery and instead draw its power directly from being plugged into a wall outlet.

The external charger 12 can contain one or more printed circuit boards 72, 74, which contain the circuitry 76 needed to implement its functionality. In one embodiment, and as shown in FIG. 2, most of the circuitry 76 can be located on an orthogonal circuit board 74, which reduces interference and heating that might be produced by the charging coil 17, as is further explained in U.S. Patent Publ. No. 20080027500. The external charger 12 also consists of a case or housing 15, typically formed of a hard plastic, which may be divided into top and bottom portions 15a and 15b connected at junction 13. The case 15 can be hand-held, or body-worn, or portable. Clamps 19 may be utilized to hold the circuit boards 72 and 74 in place mechanically, but other means may be used as well.

To wirelessly transmit energy 29 between the external charger 12 and the IPG 100, and as shown in FIG. 2, the charger 12 typically includes an alternating current (AC) coil 17 that supplies energy 29 in the form of a magnetic field to a similar charging coil 18 located in or on the IPG 100 via inductive coupling. In this regard, the coil 17 within the external charger 12 is wrapped in a plane that preferably lies substantially parallel to the plane of the coil 18 within the IPG 100. Such a means of inductive energy transfer can occur transcutaneously, i.e., through the patient's tissue 25. The energy 29 received by the IPG's coil 18 can be rectified and used to recharge battery 26 in the IPG 100, which in turn powers the electronic circuitry that runs the IPG 100. Alternatively, the energy 29 received can be used to directly power the IPG's electronic circuitry, which may lack a battery altogether. The provision of energy 29 may be controlled via the use of a simple user interface comprising, e.g., power on/off button 80 located on the exterior of the case of the external charger. Charger 12's user interface may also contain a single or multiple LED indicator lights to alert the patient of the on/off status of the charger and other relevant charger statuses, as may be desired for a given implementation.

As shown in FIG. 3, external chargers 12 may face a variety of different charging scenarios during use by a patient. Such charging scenarios may involve one or more implantable devices, with such implantable devices being implanted at varying depths and angles with respect to the charging coil 17 of the external charger 12. To further complicate the charging scenario, the implantable devices may also be located at varying distances from each other in the patient. For example, in scenario 200a shown in FIG. 3, there are two implantable devices, 100a and 100b, located a relatively small distance, D, apart from each other and having charging coils 18 oriented at offset angles of θ and θ', respectively, with respect to the surface of the patient's skin 25, and hence the charging coil 17 in the external charger 12. In some such scenarios, the power of the charging coil 17 in external charger 12 must be increased due to the inefficiency of power transfer caused by the orientation and/or the depth of the implantable devices.

In other scenarios, such as scenario 200b shown in FIG. 3, there may be a large number of implantable devices, e.g., implantable devices 100c-100g, implanted over a relatively greater distance, D'. Even if the offset angle θ" with respect to the charging coil 17 is small, it may be more desirable for the patient to use a charging coil 17 with a much larger diameter, e.g., larger than D', so that all implants may be charged simultaneously without the patient having to worry about moving the external charger.

A system has been proposed for charging an implant using an external controller to which a single external charging coil assembly can be coupled. Typically, an external controller is only used to telemeter data to and from the implant, and does not otherwise contain any means for charging the implant. This approach to implant charging is disclosed in U.S. Patent Publ. No. 20090118796 ("the '796 Publication").

The inventors believe that further improvements can be made to the versatility and design of external charging systems. The external charger 12 of FIG. 2 may not be sufficiently large or powerful enough for certain implantable device charging scenarios, as already noted. The solution of the '796 Publication requires use of the external controller to charge the implant, even though the external controller is not otherwise needed. Thus, the patient must have their external controller handy in case charging is needed, which is an inconvenience.

DETAILED DESCRIPTION

The description that follows relates to an improved external charging system that may be used by patients having various types of implantable medical device scenarios and who could benefit from improved coupling between an external device and the implanted devices, as well as improved patient comfort and convenience. For example, the present invention may be used as part of a system employing an implantable sensor, an implantable pump, a pacemaker, a defibrillator, a cochlear stimulator, a retinal stimulator, an occipital nerve stimulator, a stimulator configured to produce coordinated limb movement, a cortical and deep brain stimulator, or in any other neural stimulator configured to treat any of a variety of conditions.

This disclosure describes an external charger system comprising an external charger with an internal charging coil, as well as an output port coupleable to one of a plurality of external accessory charging coils of varying shapes and sizes. Such system may also comprise a cradle or docking station for the external charger, allowing for the use of larger accessory charging coils with greater power requirements. If the internal charging coil of the external charger is sufficient for a given patient's charging needs, the accessory charging coils may be detached from the external charger, and the external charger may serve as a standalone self-contained external charger, without the complex circuitry or interface required by typical external controllers. The external charger can automatically detect which type of a plurality of types of accessory charging coils is connected, and can adjust its operation accordingly. This versatile design allows the external charger system to be used by large numbers of patients, even if their particular implant charging scenarios are different. Accordingly, the disclosed external charger system is cheaper and simpler to manufacture when compared to manufacturing different external chargers each tailored to a particular charging scenario.

Figure 4A:
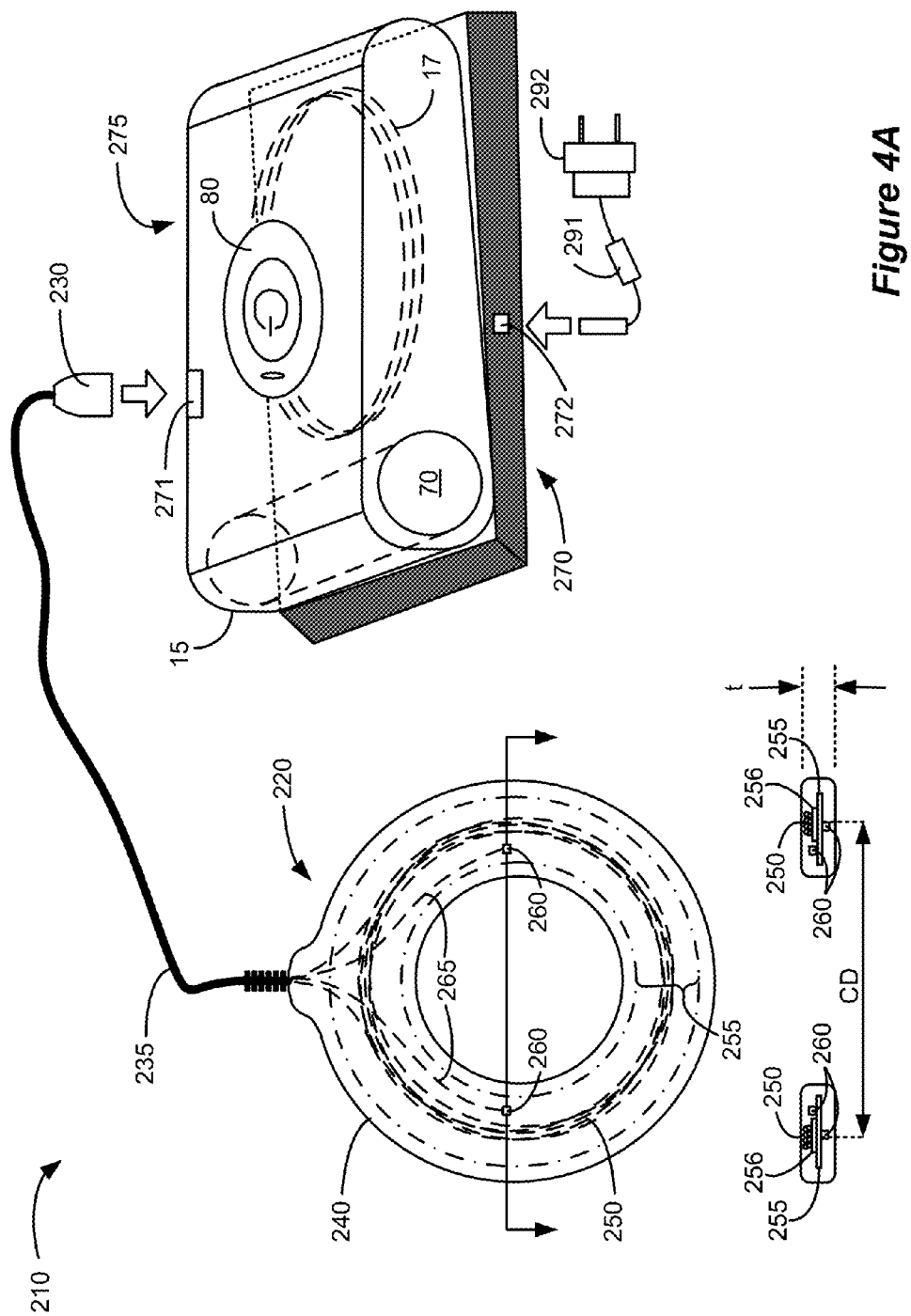
FIGS. 4A and 4B show an embodiment of an improved accessorized external charging system, comprising an external charger having an internal charging coil and a plurality of external accessory charging coils.

One embodiment of an improved accessorized external charging system 210 is illustrated in FIG. 4A. The system 210 comprises two main components: an improved external charger 275 and at least one external accessory charging coil assembly 220 that is coupleable thereto. When the accessory charging coil 220 is coupled to the external charger 275 as discussed further below, the system 210 can disable the internal charging coil 17, intelligently determine the type of accessory charging coil 220 being attached, and send power to one or more IPGs 100 via that accessory charging coil 220. As will be discussed further below, the external charger 275 may power the accessory charging coil 220 using either a rechargeable power source such as battery 70 within the external charger 275, or via a power port 272 in a cradle or docking station 270 that receives power using an AC power source 292 (e.g., a wall plug), which is rectified to DC levels by an AC-DC adapter 291. The external charger 275 controls power transmission by energizing a charging coil 250 in the accessory charging coil 220, which is otherwise devoid of its own control, power, and user interface.

Housing 15 of the external charger 275 contains a port 271 into which connectors 230 on the accessory charging coils can be placed. The connector 230 is connected by a cable 235 to a charging coil housing 240 portion that contains the charging coil 250. In the depicted example, the accessory charging coil assembly 220 is roughly donut shaped to accommodate the circular shape of the charging coil 250, but the shape can vary in other accessory charging coils, as discussed further below. For example, the charging coil housing 240 can be square shaped or even disc shaped, and can lack a central hole.

Figures 1A, 1B:
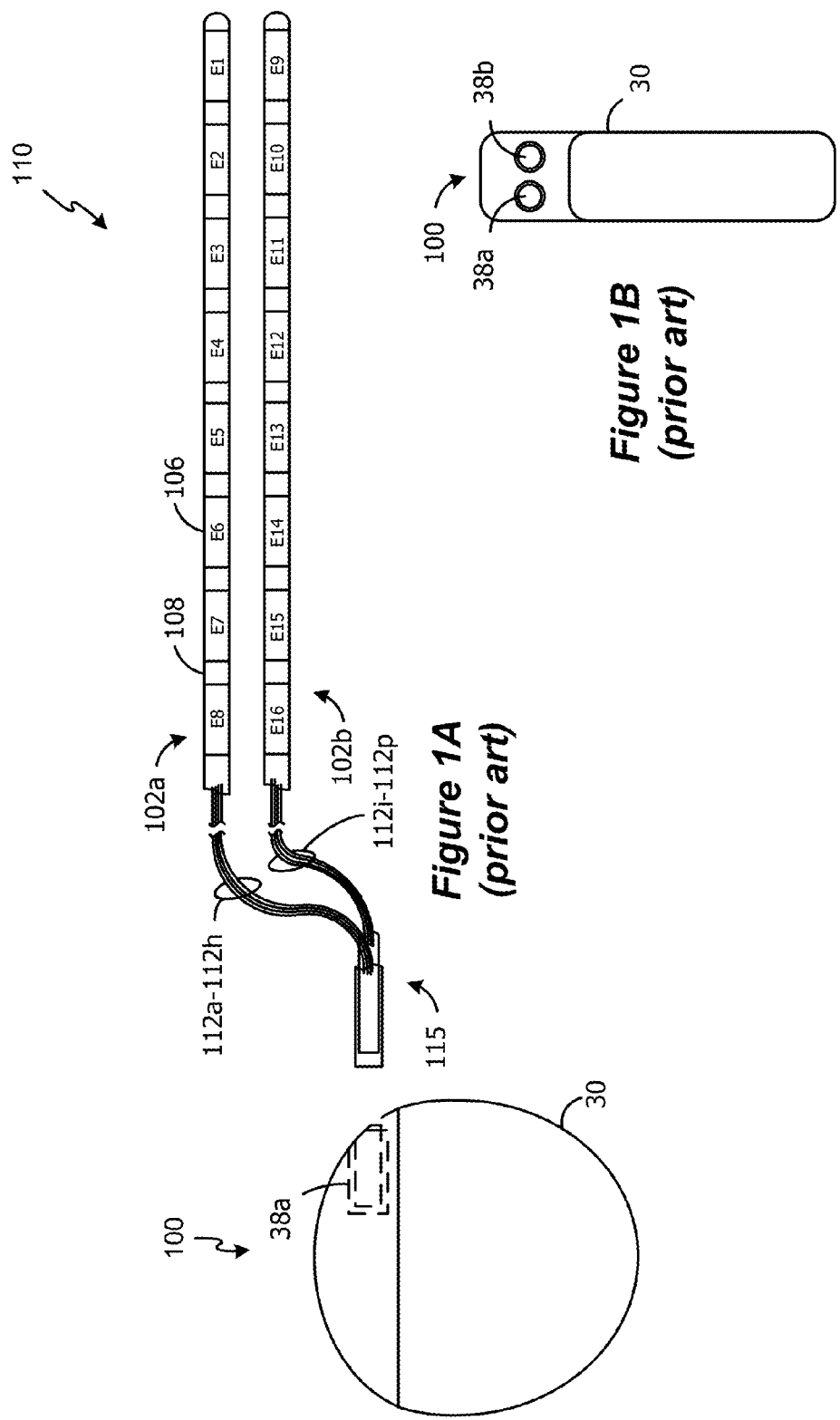
FIGS. 1A and 1B show an implantable pulse generator (IPG), and the manner in which an electrode array is coupled to the IPG, in accordance with the prior art.
Figure 2:
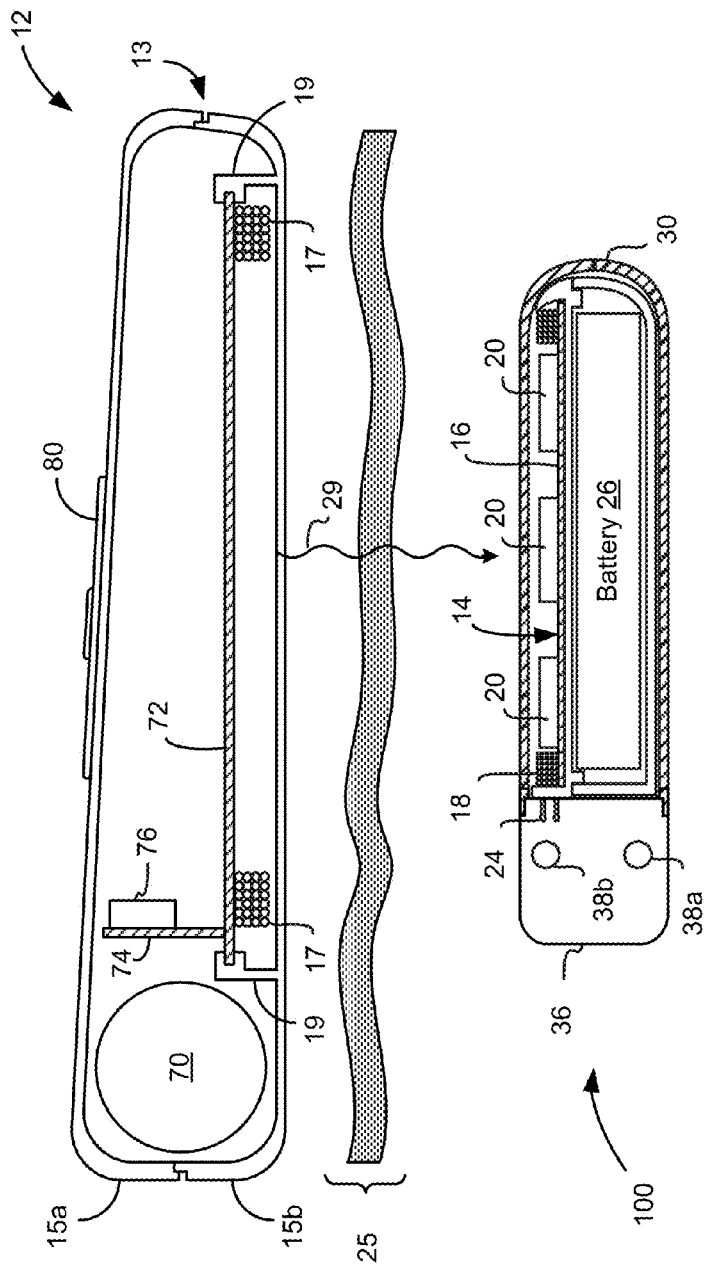
FIG. 2 shows wireless transfer of power from an external charger to the IPG, in accordance with the prior art.
Figure 3:
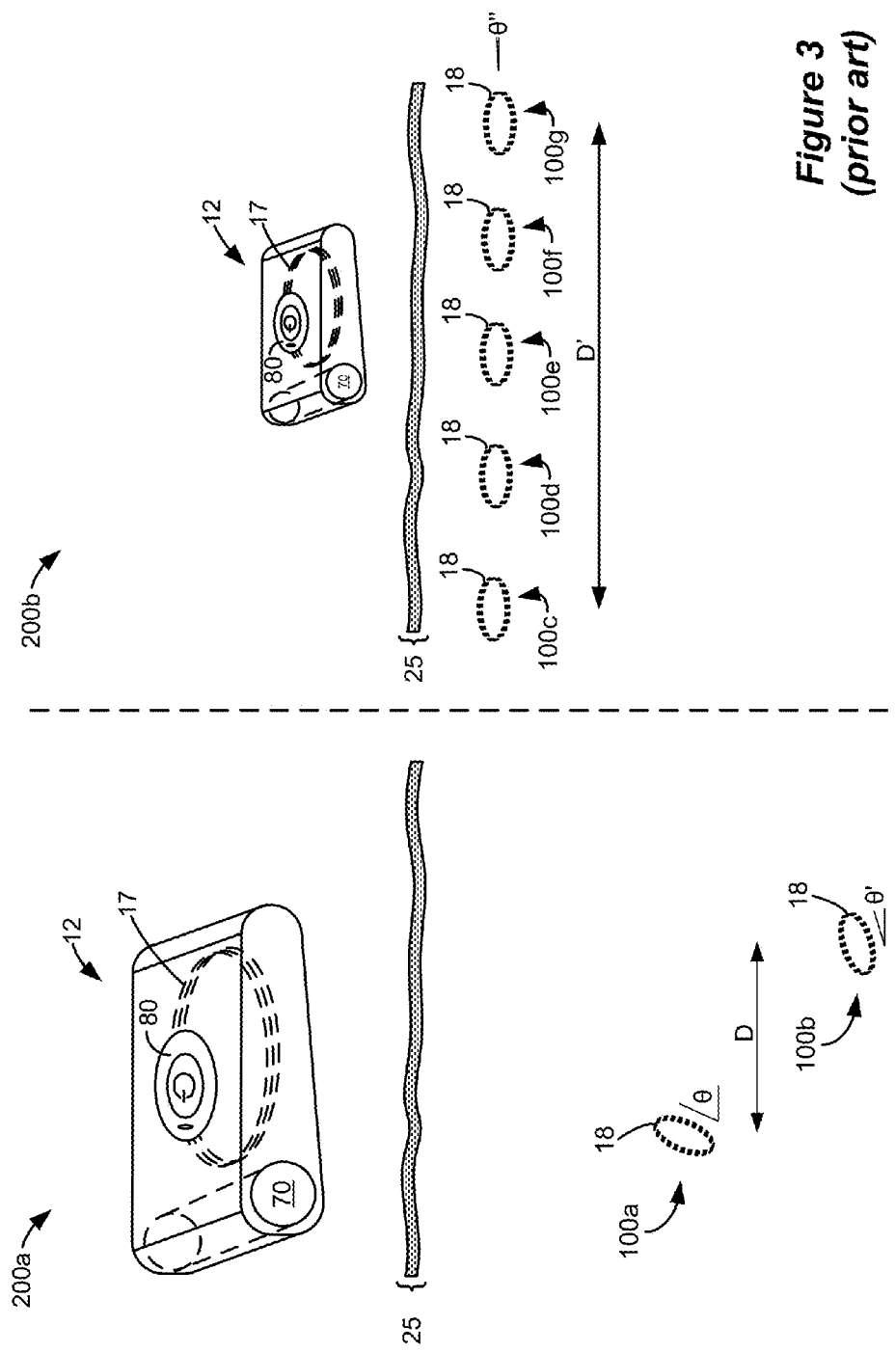
FIG. 3 shows a pair of exemplary external charger/implant scenarios, in accordance with the prior art.

The charging coil 250 in the example accessory charging coil 220 shown in FIG. 4A is preferably comprised of Litz wire, such as 25/38 Litz wire (in which each wire contains 25 individually-insulated strands of 38 gauge wire) or 50/41 Litz wire (50 individually-insulated strands of 41 gauge wire). In one example, the charging coil 250 exhibits an inductance of approximately 400 microhenries, which can be achieved by using approximately 75 turns of 25/38 Litz wire wound with a coil diameter (CD) of 5.5 cm. However, these values for the charging coil 250 are a matter of implementation choice for the designer, and can be varied for each accessory charging coil used by the system. The coil diameter (CD) is preferably made large to maximize the reliability of coupling with the corresponding charging coil 18 in the IPG (see FIG. 2). However, a larger coil diameter will require more power—a subject discussed further below.

Accessory charging coils such as external charging coil assembly 220 can be assembled in many different ways, and one method for forming a flexible external charging coil assembly is explained in detail here. As best seen in cross-section in FIG. 4A, the assembly can begin with a substrate 255 for holding electronic components, such as the charging coil 250 and temperature-sensing thermistors 260, discussed in further detail below. The substrate 255 may be flexible and comprise any type of flexible substrates used to carry electronic circuitry, such as Kapton or Polyimide. The charging coil 250 is wound to the specified number of turns, and is wound concurrently with the deposition of a silicone, such that the resulting coil 250 comprises windings in a flexible, insulative matrix of silicone. In other embodiments, a more rigid enclosure may be preferred to provide for a more robust accessory charging coil. In still other embodiments, accessory charging coils with some degree of "shape memory" may be desired for applications where the accessory charging coil is to be applied to a curved surface of the patient's body.

Also shown in the cross-sectional view of accessory charging coil 220 in FIG. 4A (but not its top-down view) is magnetic shielding material 256. Magnetic shielding material 256 may comprise, for example, a flexible ferrite material, such as the FLEX-µ FERRITE SHEET manufactured by Maruwa Co. As is explained in greater detail in U.S. Patent Publ. No. 20110234155 ("the '155 Publication"), ferrite shielding may be used to focus the magnetic field produced by the charging coil 250, i.e., to reflect a larger portion of the magnetic charging field towards the patient, which increases charging efficiency, as well as to shield electronics from the magnetic charging field produced by the charging coil 250. A flexible ferrite material may be thinner than a comparable rigid ferrite material having similar shielding properties (such as the rigid ferrite materials described in the '155 Publication), thus allowing for the construction of a thinner and more flexible coil that still promotes charging efficiency. The flexible ferrite shield could also be used in a rigid accessory charging coil to allow for a thinner assembly. As shown in the cross-sectional view, magnetic shielding material 256 may be mounted between the substrate 255 and the charging coil 250. Further, as discussed in the '155 Publication, the magnetic shielding material 256 may also be used in the external charger 275 itself to the same benefit.

Thermistors 260 may be placed on the substrate 255 and attached to appropriate lead wires 265 leading towards the cable 235. As will be discussed further below, the thermistors 260 are designed to sense the temperature during charging, i.e., when the charging coil 250 is energized, to ensure that a safe temperatures are maintained. The thermistors 260 can report the temperature back to the external charger 275, which in turn can temporarily disable further charging if the temperature is excessive (e.g., over 41 C or approximately 106 F). The actual threshold temperature will depend on the placement of the thermistors 260 and how well they correlate to the surface temperature of the accessory charging coil 220. Thermistors 260, however, are not strictly mandatory, and further can vary in number and placement around the charging coil housing 240. For example, as shown in FIG. 4A, thermistors 260 can appear on the top or bottom of the substrate 255 (as shown in the cross-sectional view in FIG. 4A) or on opposite sides of the housing 240. If the housing 240 is disk shaped, the substrate 255 can likewise be disc shaped, and the thermistors 260 could, in that arrangement, be alternatively or additionally located in the middle of the housing.

Once the electrical components are mounted to the substrate 255, the lead wires are connected to wires in the cable 235. Then, the charge coil housing 240 is mold injected around the resulting substrate 255. Silicone may be used as the fill material for the mold injection process, yielding a charge coil housing 240 that is soft and flexible. The result is a charge coil housing 240 that is comfortable and can bend to conform to the patient's body. This is especially important in applications where the patient must place weight on the housing 240 to place it in a proper alignment with an IPG 100 while charging. The charge coil housing 240 can have a thickness (t) of 3.0 mm in one example.

While the substrate 255 can be useful to stabilize the charging coil 250 and any associated electronics (e.g., temperature sensors 260) prior to mold injection of the silicone, a substrate 255 is not strictly required. Mold injection of the housing 240 to encapsulate these components can occur even without the benefit of a substrate 255.

Power to operate the external charger 275, including the power needed to energize the internal charging coil 17 and the external charging coil 250 can come from a battery 70. The battery 70 can comprise standard disposable alkaline batteries (e.g., two to four AA or AAA batteries). However, in a preferred embodiment, the battery 70 is rechargeable, which reduces battery costs and waste. In particular, a Lithium (Li)-ion battery or a Li-ion polymer battery is preferred for the battery 70. Such batteries have high cell voltages (e.g., 4.2V), such that one cell can replace numerous alkaline cells in series. Such batteries also have high energy capacity, which can be nearly twice that of alkaline cells. A rechargeable Li-ion or Li-ion polymer battery 70 thus either allows for twice the runtime of alkaline cells in the same form factor, or the same runtime with about half the package size, which enables a smaller external charger 275 design.

Alternately, the power to operate the external charger 275 may come from a wall outlet plugged into the cradle 270. The housing 15 of the external charger 275 can have two terminals 273a and 273b (see FIG. 5) allowing the coil 250 to be energized while the external charger 275 is sitting in the cradle. The external charger battery 70 in the external charger 275 may be charged simultaneously while the external charging coil 250 is energized via the cradle 270, although priority could be given to the external charging coil 250 to charge the IPG battery 26 if sufficient power to charge both batteries simultaneously is not available.

Figure 4B:
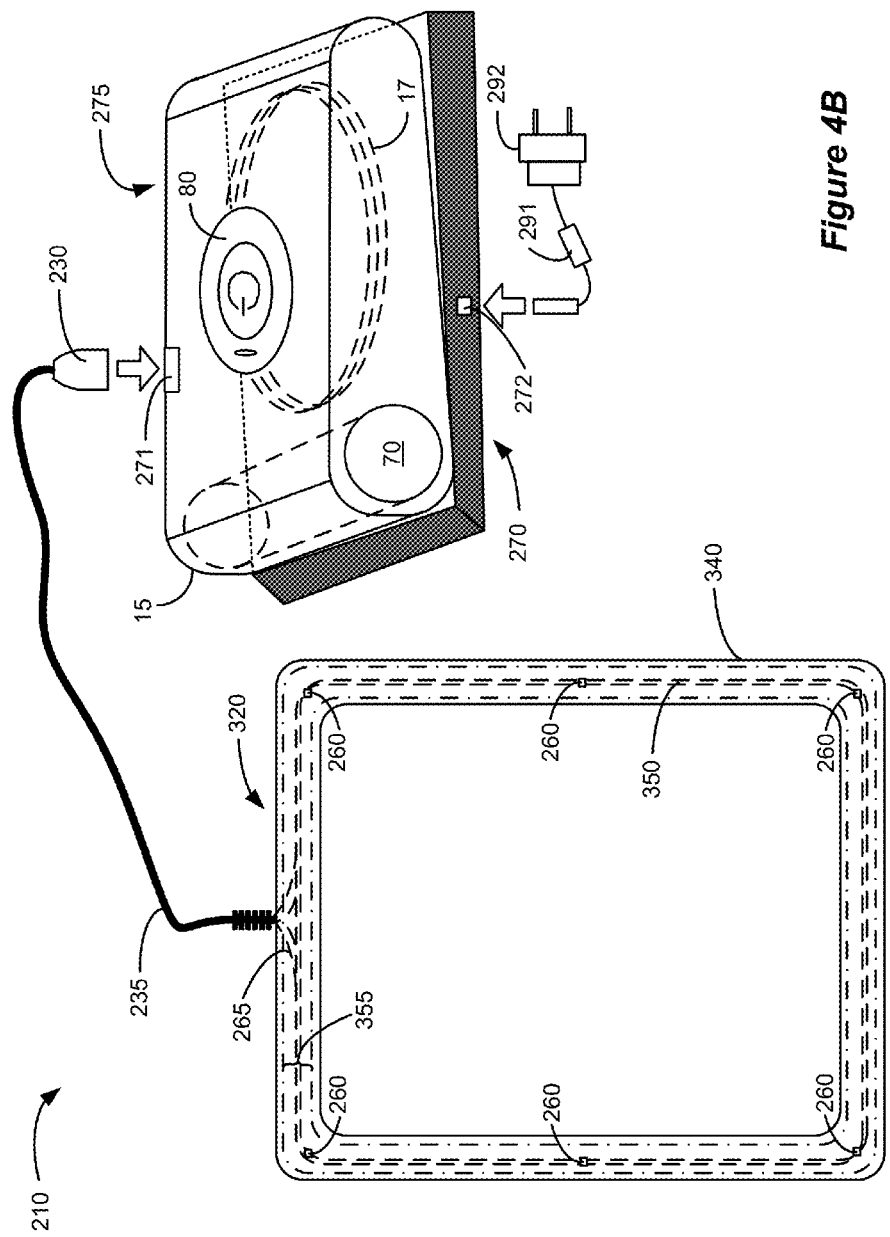

FIG. 4B illustrates system 210 with a different accessory charging coil 320 attached to the external charger 275. In FIG. 4B, the external charging coil assembly 320 comprises a large rectangular coil 350, with a cross-sectional width (e.g., 6 in.) and length (e.g., 10 in.) each larger than the diameter of the accessory charging coil 220 shown in FIG. 4A, as well as a larger substrate 355, housing 340, and potentially a magnetic shielding material (not shown). A larger accessory charging coil 320 may be desirable for use in charging for patients having deeply-implanted stimulators (e.g., approximately 12 cm deep) or in patients having a larger number of implants spread over a relatively large area. Charging with a larger accessory charging coil 320 may be more beneficial to some patients because it allows for the charging field to penetrate more deeply through the patient's tissue and provides a larger area of coverage.

With larger coil sizes, however, come greater power requirements. In one embodiment, accessory charging coil 320 may draw approximately 4 watts of power. To avoid draining battery 70 too rapidly, charging with accessory charging coil 320 may preferably take place with the external charger 275 sitting in the cradle 270 and drawing power directly from a wall outlet via wall plug 292. If necessary, accessory charging coil 320 may have a longer cable 235 to accommodate the requirement that the external charger 275 and cradle 270 be located proximate to a wall plug.

Larger coil sizes may also present more complex heating concerns. As such, a greater number of thermistors 260 (e.g., six) are placed around external charging coil assembly 320 than were shown in external charging coil assembly 220 (two) of FIG. 4A. In a preferred embodiment, thermistors 260 are spaced substantially evenly around the external charging coil assembly 320, allowing the temperature at various locations of external charging coil assembly 320 to be monitored by external charger 275. This may be important because "hot spots" may develop at various places around external charging coil assembly 320 caused by a variety of factors. Reading out values from the thermistors 260 and adjusting charging accordingly can be difficult given interference created by the relatively strong magnetic field produced by the charging coil 350. Thus, in one embodiment, the external charging coil 350 is temporarily disabled while reading out data from the thermistors 260. The thermistors 260 can be read sequentially at approximately thirty second intervals. Although not shown in FIG. 4B, the accessory charging coil 320 may also include a heat-conductive material, e.g., a thermal pad, to evenly distribute heat and to mitigate problems caused by hot spots developing in the accessory charging coil 320 during use.

Figure 5:
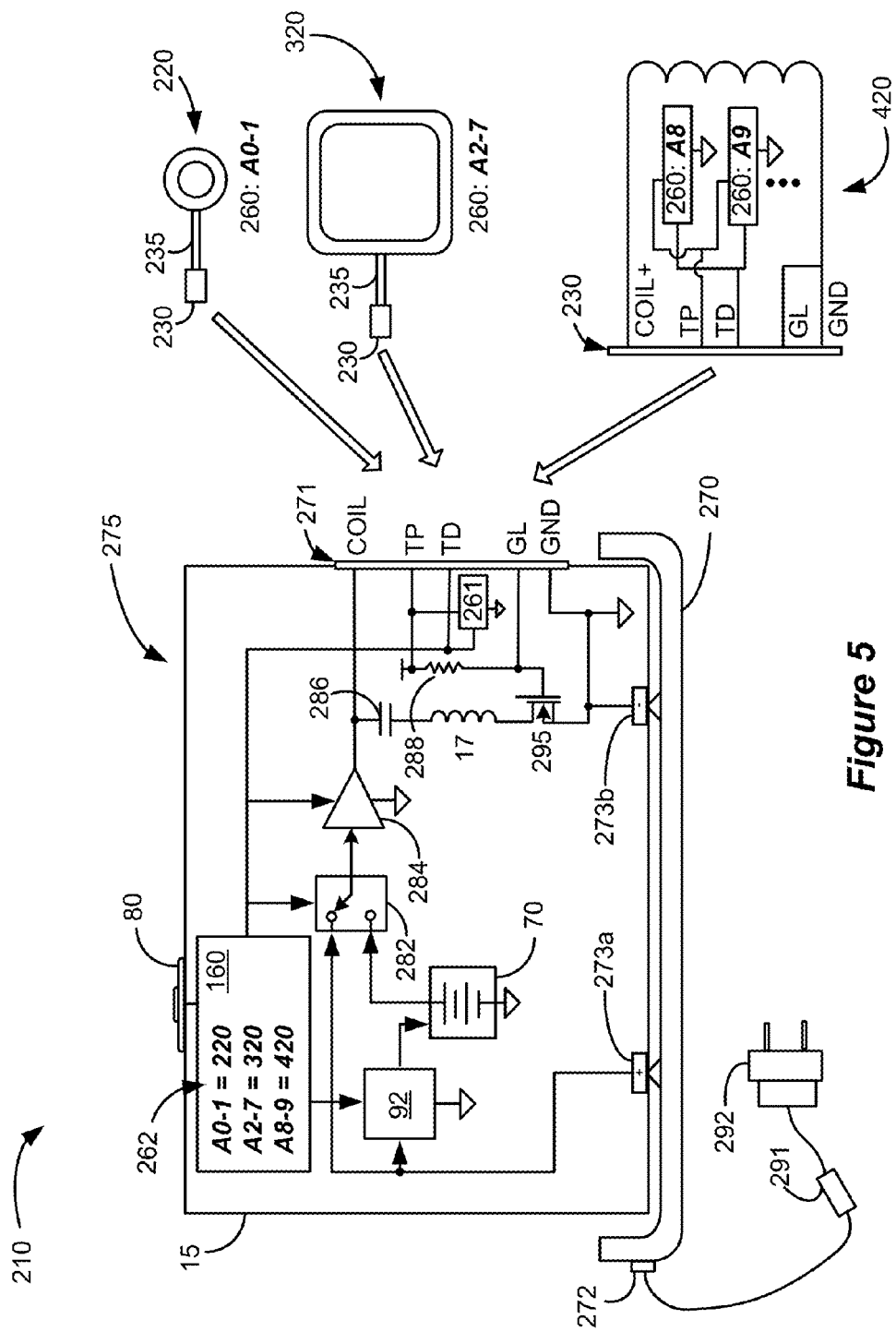
FIG. 5 shows a circuit schematic of the improved accessorized external charger system, according to one embodiment.

Turning now to FIG. 5, a circuit schematic of the accessorized external charger system 210 is shown in greater detail, including the accessory charging coils 220 and 320 of FIGS. 4A and 4B. An additional accessory charging coil 420 is shown to illustrate the basic circuitry present in each of the accessory charging coils.

As mentioned previously, the external charger 275 has an internal coil 17 and can be used as a stand-alone cordless external charger for charging an IPG battery. External charger 275 also comprises battery 70 and battery charging circuitry 92, which charges battery 70 in a controlled fashion. Microcontroller 160 is used to control the various elements of external charger 275, including switch 282 and coil driver 284. (Microcontroller 160 can comprise integrated or non-integrated circuitry capable of processing logic in a computer system). Switch 282 switches the source of power for the coil driver 284 between the battery 70 and the DC voltage provided by the cradle 270 at contacts 273a and 273b. As mentioned above, for larger coils requiring larger power draws, the external charger 275 may preferably (or even necessarily) operate with the power provided by the cradle 270. If the external charger 275 is not receiving power from the cradle 270, then it may necessarily need to rely on battery 70 to power the coil driver 284.

The accessorized external charger system 210 is able to determine whether an accessory charging coil has been inserted into port 271 on the external charger 275. Port 271 may comprise any number of well-known circular barrel connectors having a sufficient number of connector pins. In one embodiment, the port 271 has five connections: coil power (COIL), thermistor power (TP), thermistor data (TD), ground (GND), and a ground loopback (GL) signal. The GL signal 274 is shorted to GND in the accessory charging coils, as shown in coil 420. When an accessory charging coil is connected to the external charger 275, GL is grounded through this short, which grounds the gate of switch 295 in the external charger 275 and turns it off, which disconnects the internal charging coil 17. By contrast, when no accessory charging coil is connected, the gate of switch 295 is pulled high through pull-up resistor 288, which turns on the switch 295 and connects the internal charging coil 17 and its tuning capacitor 286 to the coil driver 284. In this way, the external charger 275 will drive an accessory charging coil if it is attached to port 271, and otherwise will drive its own internal charging coil 17.

Also shown in FIG. 5 is an internal thermistor 261, which receives thermistor power (TP) and reports the external charger 275's temperature to the microcontroller 160 along the thermistor data signal TD. Shown in example accessory charging coil 420 are the external thermistors 260, which likewise receive power (TP) and report external temperatures via TD. Thermistors 261 and 260 can comprise Maxim DS1825 digital thermistors provided by Dallas Semiconductor. The DS1825 requires only one wire (TD) for communication, and each thermistor may store a unique 64-bit serial code in its on-board ROM. The DS1825 can also be programmed with a 4-bit address, thus allowing up to sixteen thermistors to be uniquely programmed via the single wire (TD). The one-wire communication feature of the DS1825 allows each of the external thermistors 260 to share the same power, data, and ground signals, allowing the use of multiple thermistors with only three wires.

It may also be advantageous to programming the addresses of the thermistors 260 in order to allow the external charger 275 to be able to determine which type of accessory charging coil (e.g., 220, 320, or 420) has been connected so that charging parameters may be set appropriately. In this regard, assume as shown in FIG. 5 that accessory charging coil 220 contains two thermistors 260 which have been programmed with addresses 0 (i.e., '0000') and 1 (i.e., '0001'). Assume further that that accessory charging coil 320 contains six thermistors 260 which have been programmed with addresses 2-7 (i.e., '0010' to '0111'). Assume still further that that accessory charging coil 420 contains two thermistors 260 which have been programmed with addresses 8 (i.e., '1000') and 9 (i.e., '1001'). Knowing this, a table 262 can be stored in or accessible to the microcontroller 160 that associates each address with a particular type of accessory charging coil. Thus, table 262 reflect that addresses 0 and 1 correspond to the smaller, circular accessory charging coil 220; that addresses 2-7 correspond to the larger, rectangular accessory charging coil 320; and that addresses 8 and 9 correspond to accessory charging coil 420, etc.

When it has been detected that an accessory charging coil has been connected to the external charger 275 (e.g., as described earlier), the microprocessor 160 can thus query the various addresses of the thermistors via signal line TD. If no acknowledgment or temperature is reported from a thermistor 260 having a programmed address of 0 or 1 for example, then the microcontroller 160 would know that accessory charging coil 220 has not been connected. If, by contrast, an acknowledgment or temperature is reported back for thermistors having programmed addresses ranging from 2-7, then the microcontroller 160 would know that the larger accessory charging coil 320 has been connected, and can control the charging process to be carried out by that coil accordingly. For example, in the case that larger coil 320 is detected, the microcontroller 160 could increase the power provided by the coil driver 284; could limit the power used to drive that coil to that provided by the cradle 270; could change the safety temperature set point as appropriate for that coil, etc.

It should be noted that, while it is easy and expedient to use the addressing feature of the disclosed thermistors as a means of identifying and controlling the various accessory charging coils, this is merely an exemplary scheme. Other schemes could likewise be used to allow the external charger to determine the type of the accessory charging coils that are connected to it. For example, each of the accessory charging coils 220, 320, 420, etc., could contain programmable memory, fuses, or antifuses defining the address of the coil. These addresses could then be queried in standard ways to inform the external charger 275 of the particular type of accessory charging coil that has been connected, and to control that coil accordingly. Furthermore, the 64-bit serials codes of each of the thermistors 260 can also be read and stored in the external charger 275, and likewise populated in table 262 to determine the accessory charging coil at issue.

In a more sophisticated embodiment, the external charger 275 could alert the patient if the type of attached accessory coil does not match an entry in its table 262, which may prevent a patient from using an accessory charging coil that is improper for their particular implantable device scenario.

The disclosed improved external charger system thus uses a single external charger 275 to drive a wide variety of types of accessory charging coils through port 271. The exemplary accessory coils shown in FIG. 5 can provide the accessorized external charger system 210 with capabilities not available with a standalone, dedicated external chargers according to the prior art. For example, small coil assembly 220 (FIG. 4A) may comprise a smaller, thinner coil, allowing for more comfortable charging in situations involving a single implant, or where the patient cannot easily or comfortably hold the entire external charger against their body for long periods of time. Small coil assembly 220 may have a diameter of approximately 7 cm and a power requirement of 1 W. Large coil assembly 320 may provide for better charging in scenarios in which there is a greater number of implants requiring a larger cover area, or in scenarios in which the implants are more deeply implanted and a stronger external charging field is desired. It may have dimensions of approximately ten inches by six inches and have a power requirement of approximately 4 W. An Occipital Nerve Stimulation (ONS) accessory charging coil (not shown) may be made of a flexible material capable of being formed into a curved shape to conform to the back of a patient's neck where such implants would be naturally located, and may have a power requirement of approximately 2 W.

Thus, the improved accessorized external charger system 210 may be used by a wide variety of patients, e.g., patients receiving SCS, DBS, or ONS therapies, with a given patient only needing to purchase and use the accessory charging coil corresponding to his or her own particular implantable device scenario. Alternately, some patients may use only the standalone portable external charger 275, and may not require an accessory charging coil for their charging needs. The manufacturer of the system is further convenience by the need to manufacture only a single external charger 275 to work in the system 210, rather than designing unique external chargers for each and every implantable medical device scenario.

Figure 6:
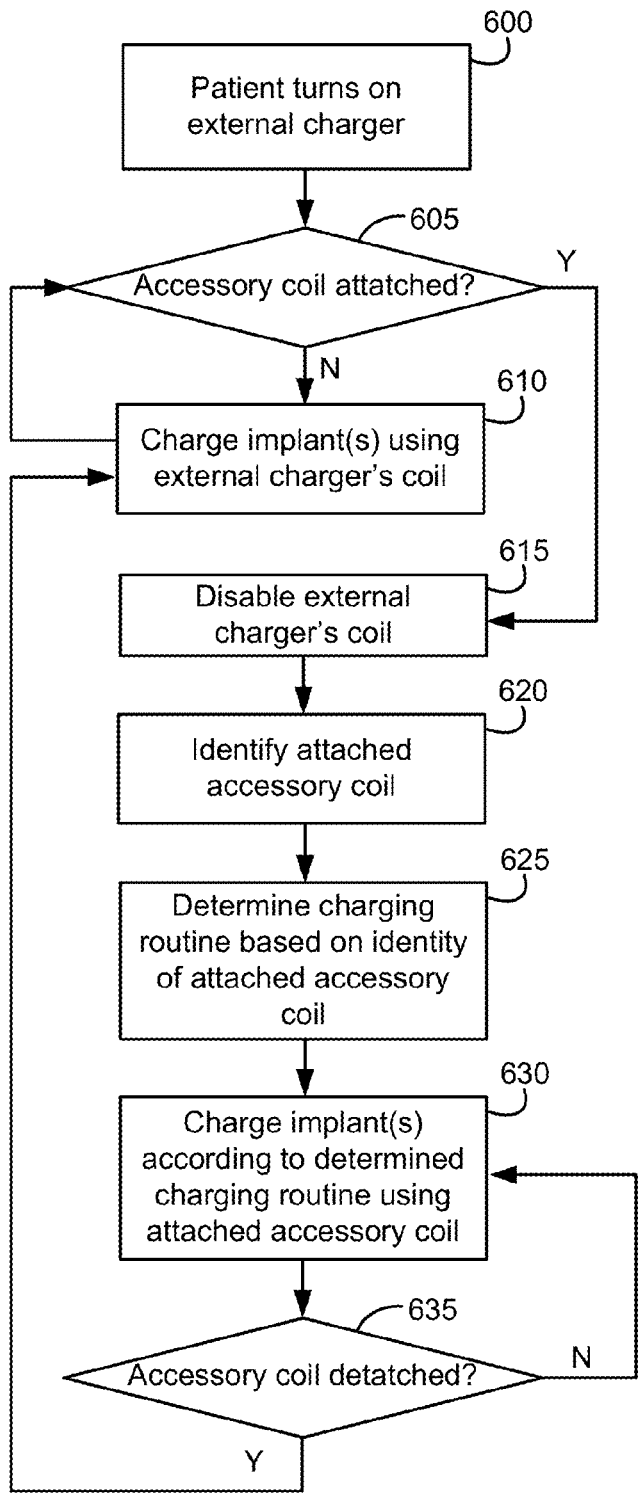
FIG. 6 shows a flowchart detailing the operation of the improved accessorized external charger system, according to one embodiment.

Turning now to FIG. 6, a flowchart detailing the operation of the improved accessorized external charger system 210 is shown. First, the patient turns on the external charger 275 to initiate a charging session (Step 600). Next, the external charger 275 determines whether or not there is an accessory charging coil coupled to the external charger (Step 605). If so, the system will disable the external charger's internal charging coil 17 (Step 615), identify the type of accessory charging coil that is attached (Step 620), and determine a charging routine and parameters based on the identity of the attached accessory charging coil (Step 625). Next, the system 210 will charge the implantable medical device(s) via the connected accessory charging coil according to the determined charging routine for that accessory coil (Step 630). Periodically during the charging session, the system 210 will determine whether the accessory charging coil has been detached (Step 635). If not, the system 210 will continue to charge the implantable medical device(s) (Step 630). If the accessory charging coil has been detached, the system 210 may begin to charge using the external charger's internal charging coil 17 (Step 610). Alternately, the system 210 may suspend charging entirely when the accessory charging coil has been detached (not shown in FIG. 6).

Returning to Step 605, if it is initially determined by the external charger 275 that there is no accessory charging coil attached, the external charger may begin to charge using the external charger's internal charging coil 17 (Step 610) and continuing charging as such, periodically checking to determine whether an accessory charging coil has subsequently been attached (Step 605), in which case the system 210 may begin to charge using such accessory coil (Steps 615-630) as just discussed.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger system for providing power to one or more implantable medical devices, comprising:
   an external charger comprising an internal first charging coil configured to selectively provide a first field to provide power to the one or more implantable medical devices; and
   an external charging coil assembly comprising a second charging coil configured to selectively provide a second field to provide power to the one or more implantable medical devices,
   wherein the external charging coil assembly is attachable to and detachable from the external charger.

2. The system of claim 1, wherein the external charger is hand-held and portable.

3. The system of claim 1, wherein the external charging coil assembly is attachable to and detachable from the external charger at a port on the external charger.

4. The system of claim 1, wherein the external charging coil assembly is flexible.

5. The system of claim 1, wherein the external charging coil assembly is rigid.

6. The system of claim 1, wherein the external charger further comprises a coil driver configured to energize the first charging coil and the second charging coil of the external charging coil assembly to respectively produce the first and second fields.

7. The system of claim 6, wherein the coil driver is configured to energize the first coil with a first power, and to energize the second coil with a second power different from the first power.

8. The system of claim 1, wherein the external charger system is configured to provide the first field to the one or more implantable medical devices using the first coil if no external charging coil assembly is attached to the external charger.

9. The system of claim 8, wherein the external charger system is configured to provide the second field to the one or more implantable medical devices using the second charging coil if the external charging coil assembly is attached to the external charger.

10. The system of claim 1, wherein the external charging coil assembly comprises at least one thermistor.

11. The system of claim 10, wherein at least one of the thermistors is used to encode an address for the external charging coil assembly.

12. The system of claim 1, wherein the external charger further comprises a microcontroller for automatically determining whether the external charging coil assembly is attached to or detached from the external charger.

13. The system of claim 12, wherein the microcontroller determines whether the external charging coil assembly has been attached to the external charger by reading at least one address from the external charging coil assembly.

14. The system of claim 12, wherein the microcontroller adjusts operation of the system depending whether the external charging coil assembly is attached to or detached from the external charger.

15. The system of claim 14, wherein the external charger further comprises
a coil driver configured to energize the first charging coil if the external charging coil assembly is detached from the external charger, or the second charging coil of the external charging coil assembly if the external charging coil assembly is attached to the external charger,
wherein adjusting the operation of the system comprises adjusting a power provided by the coil driver.

16. The system of claim 14, wherein adjusting the operation of the system comprises adjusting a temperature set point.

17. The system of claim 1, wherein the external charging coil assembly comprises at least one address recognizable by the external charger.

18. The system of claim 1, wherein the external charger further comprises a user interface and a battery.

19. The system of claim 18, further comprising a cradle, wherein the cradle is configured to charge the battery in the external charger.

20. The system of claim 19, wherein the cradle is further configured to provide power to the external charger, and wherein the power provided to the external charger can be used to produce the second field of the external charging coil assembly.

21. The system of claim 20, wherein the second field of the external charging coil assembly is produced using either the power provided to the external charger or the battery.

22. The system of claim 1, wherein the external charging coil assembly further comprises a magnetic shielding material for focusing the second field to the one or more implantable medical devices.

23. A method for providing power to one or more implantable medical devices with an external charger system, comprising:
   determining whether an external charging assembly is coupled to an external charger;
   if the external charging assembly is not coupled to the external charger, wirelessly providing a first field to provide power to the one or more implantable medical devices from the external charger; and
   if the external charging assembly is coupled to the external charger, wirelessly providing a second field to provide power to the one or more implantable medical devices from the coupled external charging assembly.

24. The method of claim 23, wherein the first field is produced by a first coil in the external charger.

25. The method of claim 24, wherein the second field is produced by a second coil in the external charging assembly.

26. The method of claim 23, further comprising, as an initial step, initiating the external charger to provide power to the one or more implantable medical devices.

27. The method of claim 26, wherein initiating the external charger comprises receiving a selection at a user interface on the external charger.

28. The method of claim 23, wherein the power provided to the one or more implantable medical devices is adjusted by the external charger depending whether the external charging assembly is coupled to the external charger or not.

29. The method of claim 28, wherein an intensity of the power provided to the one or more implantable medical devices is adjusted.

30. The method of claim 23, wherein a temperature set point is adjusted by the external charger depending whether the external charging assembly is coupled to the external charger or not.

31. The method of claim 23, wherein the external charger comprises a port for coupling to the external charging assembly.

32. The method of claim 23, further comprising reading an address of the external charging assembly at the external charger if the external charging assembly is coupled to the external charger.

33. The method of claim 23, wherein the power provided to the one or more implantable medical devices by the first and second fields is provided by a battery in the external charger.

34. The method of claim 23, wherein power provided to the one or more implantable medical devices by the first and second fields is provided by an AC power source coupled to the external charger.

\* \* \* \* \*